(12) United States Patent
Jonas

(10) Patent No.: US 6,528,662 B2
(45) Date of Patent: Mar. 4, 2003

(54) PROCESS FOR THE PREPARATION OF 3, 4-ALKYLENEDIOXYTHIOPHENE-2,5-DICARBOXYLIC ACID DERIVATIVES

(75) Inventor: Friedrich Jonas, Aachen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/877,301

(22) Filed: Jun. 8, 2001

(65) Prior Publication Data
US 2002/0002287 A1 Jan. 3, 2002

(30) Foreign Application Priority Data
Jun. 13, 2000 (DE) .......................... 100 29 075

(51) Int. Cl.$^7$ .......................... C07D 495/02
(52) U.S. Cl. .......................... 549/50
(58) Field of Search .......................... 549/50

(56) References Cited

U.S. PATENT DOCUMENTS

| | | | |
|---|---|---|---|
| 4,910,645 A | 3/1990 | Jonas et al. | 340/525 |
| 4,959,430 A | 9/1990 | Jonas et al. | 339/257 |
| 4,987,042 A | 1/1991 | Jonas et al. | 339/213 |
| 5,035,926 A | 7/1991 | Jonas et al. | 339/393.1 |
| 5,300,575 A | 4/1994 | Jonas et al. | 440/186 |
| 5,599,522 A * | 2/1997 | Jorgensen et al. | |

OTHER PUBLICATIONS

Kumar, et al, 1998, Chem, Meter., 10, 896–902.*
Polymer, Bd. 35, Nr. 7, (month unavailable) 1994, XP001025972, Schema 1, Seite 1348, Spalte 1. Absätze 3,4, Q. Pei, et al, "Electrochromic and highly stable poly(3,4–ethylenedioxythiophene) switches between opaque blue–black and transparent sky blue".
Macromolecules, American Chemical Society, Easton, US, Bd. 30, Nr. 9, May 5, 1997, Seiten.
2582–2588, XP000688333, ISSN: 0024–9297, Seite 2582, Spalte 2, Absatz 3–Seite 2583, Spalte 1, Absatz 1, Seite 2586, Spalte 2, Absatz 6, Seite 2587, Spalte 1, Absatz 4, B. Sankaran et al, "High–contract electrochromic polymers from alkyl–derivatized poly(3,40ethylenedioxythiophenes)".
Synthetic Metals, Elsevier Sequoia, Lusanne, CH, Bd. 93, (month unavailable) 1998, Seiten 33–41.
XP000995602, ISSN: 0379–6779, Schema 1, Seite 34, Spalte 2, Absatz 3, Seite 35, Spalte 1, Absatz 4, A. Lima et al, "Electropolymerization of 3,4–ethylenedioxythiophene and 3,4–ethylenedioxythiophene methanol in the presence of dodecylbenzenesulfonate".
Tetrahedron, vol. 23, (month unavailable) 1967, pp. 2437–2441, V. N. Gogte et al, Synthesis of Potential Anti-cancer Agents—I Synthesis of Substituted Thiophenes.

* cited by examiner

Primary Examiner—Joseph K. McKane
Assistant Examiner—Andrea D. Small
(74) Attorney, Agent, or Firm—Godfried R. Akorli; Diderico van Eyl

(57) ABSTRACT

A process for the preparation of 3,4-alkylenedioxythiophene-2,5- dicarboxylic acid derivatives selected from the group consisting of compounds of the general formulae IV and V:

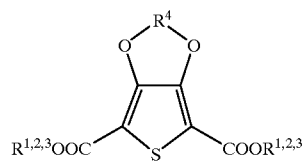

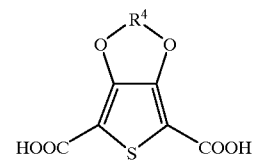

comprising carrying out at least 2 steps in accordance with formula scheme 1 without isolation of intermediates, wherein $R^1$, $R^2$, $R^3$ and $R^4$ are identical or different and are a linear or branched, optionally substituted alkyl radical having 1 to 20 carbon atoms, A is lithium, sodium or potassium, and Hal is fluorine, chlorine, bromine or iodine, wherein the formula scheme 1 comprises:

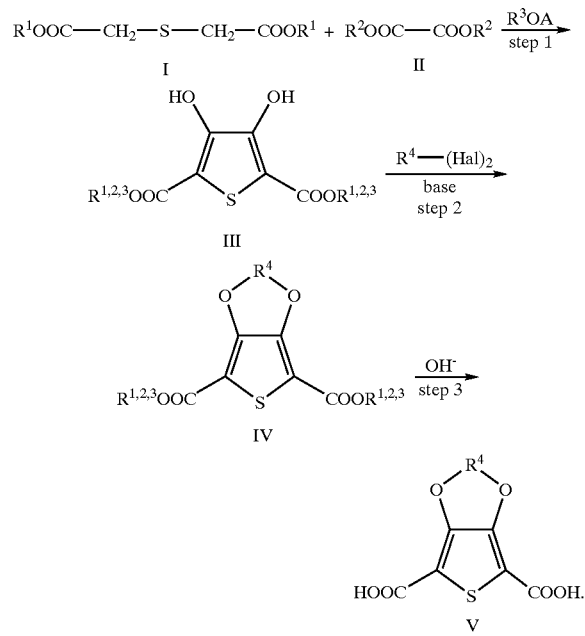

5 Claims, No Drawings

PROCESS FOR THE PREPARATION OF 3,4-ALKYLENEDIOXYTHIOPHENE-2,5-DICARBOXYLIC ACID DERIVATIVES

BACKGROUND

Organic conductive polymers have in recent times become more and more widespread in industry. Areas of application are, for example, the through-plating of circuit boards (EP-A-553671), antistatic finishing of photographic films (EP-A-440957) or as electrode in solid electrolyte capacitors (EP-A-340512). Particular importance in these areas has been achieved by poly-3,4-alkylenedioxythiophenes (EP-A-339340), which are distinguished by high stability and electrical conductivity. The monomeric 3,4-alkylenedioxythiophenes necessary for the preparation can in principle be prepared by processes known from the literature. One synthesis is described, for example, in Gogte et al., Tetrahedron 23 (1967) 2437. Starting from thiodiacetic acid diesters I and oxalic acid diesters II, 3,4-dihydroxythiophene-2,5-dicarboxylic acid esters III are prepared in accordance with formula scheme I in the presence of alkali metal alkoxides (step 1). These esters III are then alkylated using dihaloalkanes to give 3,4-alkylenedioxythiophene-2,5-dicarboxylic acid esters IV (step 2), which are saponified to give the 3,4-alkylenedioxythiophene-2,5-dicarboxylic acids V (step 3) and decarboxylated to give the monomeric 3,4-alkylenedioxythiophenes. The isolation of the individual intermediates which has hitherto been carried out in the prior art is complex and expensive.

Formula Scheme 1

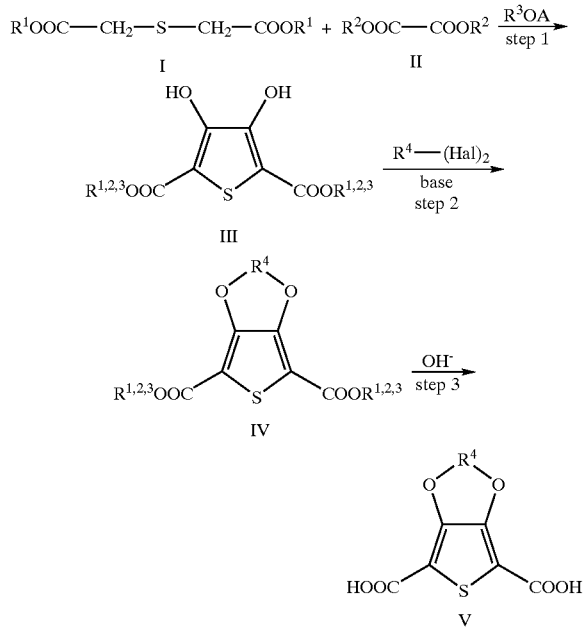

In formula scheme 1:
$R^1, R^2, R^3$ and $R^4$ are identical or different and are a linear or branched, optionally substituted alkyl radical having 1 to 20 carbon atoms,
A is lithium, sodium or potassium, and
Hal is fluorine, chlorine, bromine or iodine.

Surprisingly, it has now been found that steps 1 and 2 or 2 and 3 or 1 to 3 can be carried out without isolation of the intermediates while obtaining the target products in high purity and yield.

DESCRIPTION

The invention therefore relates to a simple process for the preparation of 3,4-alkylenedioxythiophene-2,5-dicarboxylic acids or their esters by combining individual synthesis steps without isolation of the intermediates.

The process is described in greater detail below. When combining steps 1 and 2, the following procedure is followed:

In step 1, the condensation of the thiodiacetic acid esters with oxalic acid esters is carried out in the presence of alkali metal alkoxides. Suitable metal alkoxides are the alkoxides of lithium, sodium and potassium, preferably sodium or potassium, which are derived from linear or branched aliphatic alcohols. Preferred alcohols are methanol, ethanol, isopropanol, n- and isobutanol and tert-butanol.

The reaction is preferably carried out in solution. Suitable solvents are lower aliphatic alcohols, such as methanol, ethanol, isopropanol, n- and isobutanol and tert-butanol. Preference is given to the alcohol which is also present in the alkoxide component. Thiodiacetic acid esters and oxalic acid esters are usually employed in equimolar amounts. Based on 1 mol of the esters, from 2.0 to 4.0 mol of alkoxide, preferably from 2.0 to 3.0 mol of alkoxide, particularly preferably from 2.0 to 2.5 mol of alkoxide, are used.

The reaction is carried out at from −10° C. to 200° C., preferably from 0° C. to 100° C., particularly preferably from 10° C. to 70° C.

The reaction time is from 10 minutes to 24 hours, preferably from 1 hour to 8 hours.

The alkoxide is preferably initially introduced and the esters added dropwise with stirring, either separately or as a mixture.

After completion of the reaction, any excess of alkoxide is neutralized by addition of acids or acidic salts, such as alkali metal hydrogensulphates.

For carrying out the 2nd step, a higher-boiling solvent, preferably having a boiling point of from 100° C. to 300° C., is then added. Examples of suitable solvents are linear or cyclic amidic solvents, such as N-methylpyrrolidone, N,N-dimethylformamide, N,N-dimethylacetamide, aliphatic sulphoxides or sulphones, such as dimethyl sulphoxide or sulpholane. The solvents can be used alone or as mixtures.

After addition of the higher-boiling solvents, the alcohol is distilled off, if necessary under reduced pressure. Subsequently, in a preferred embodiment, a base is added in an amount of from 0.01 to 0.5 mol, based on 1 mol of the esters employed. Preferred bases are sodium carbonate and potassium carbonate. Particular preference is given to potassium carbonate.

The ring closure to give the 3,4-alkylenedioxythiophenedicarboxylic acid ester is then carried out by reaction of the alkali metal salts of the 3,4-dihydroxydicarboxylic acid esters with alkylating agents. Suitable alkylating agents are dihaloalkanes. Preference is given to dichloro- or dibromoalkanes. Particular preference is given to linear 1,2-dihaloalkanes having 2 to 18 carbon atoms and 1,3-dihaloalkanes having 3 to 18 carbon atoms (halogen is identical or different and is fluorine, chlorine, bromine or iodine). Particular preference is given to 1,2-dichloroethane and 1,2-dichlorohexadecane.

The reaction is carried out at temperatures of from 50 to 200° C., preferably at from 100 to 150° C., if desired under pressure. The reaction duration is from 1 to 24 hours.

When the reaction is complete, the 3,4-alkylenedioxythiophenedicarboxylic acid ester is isolated by removal of the solvent by distillation, if necessary under reduced pressure, and/or precipitation using water. The crude product can subsequently be dried or saponified directly in the moist state to give the free 3,4-alkylenedioxythiophenedicarboxylic acid.

In a particular embodiment of the invention, the 3,4-ethylenedioxythiophene-dicarboxylic acid ester is not isolated, with incorporation of step 3. When the alkylation is complete, the majority of the solvent is distilled off, if necessary under reduced pressure, and the 3,4-ethylenedioxythiophenedicarboxylic acid ester is subsequently saponified directly using bases.

The saponification is preferably carried out using alkali metal hydroxides, which are used as a solution in water and/or as a mixture with water-miscible aliphatic alcohols. Examples of suitable alcohols are methanol, ethanol and isopropanol. The saponification can be carried out at room temperature or at temperatures above room temperature. It has proven successful to carry out the saponification at the reflux temperature of the water or the water/alcohol mixture. When the saponification is complete, the free 3,4-ethylenedioxythiophenedicarboxylic acid is liberated and precipitated by addition of mineral acids. The product is subsequently isolated by suction filtration and dried.

In a further embodiment, steps 2 and 3 are combined. In order to carry out the 2nd step, the separately prepared 3,4-dihydroxythiophene-2,5-dicarboxylic acid ester is initially introduced in the solvents described above. As base, from 1.0 to 1.5 mol, preferably from 1.1 to 1.4 mol, of alkali metal carbonate are added, based on 1 mol of 3,4-dihydroxythiophene-2,5-dicarboxylic acid ester. Preference is given to potassium carbonate.

The further reaction to give the 3,4-alkylenedioxythiophenedicarboxylic acid ester and saponification to give the 3,4-alkylenedioxythiophenedicarboxylic acid are carried out as described above under the combination of steps 1 to 3.

The invention is further described in the following illustrative examples in which all parts and percentages are by weight unless otherwise indicated.

EXAMPLE 1

3,4-Ethylenedioxythiophene-2,5-dicarboxylic Acid Ester Mixture of Dimethyl, Methyl Ethyl and Diethyl Esters (Combination of the 1st and 2nd steps)

848 g of 32% potassium methoxide solution (3.88 mol) and 200 g of methanol are introduced into a 6 l apparatus with plane ground joints, fitted with a gate-impeller stirrer, reflux condenser, thermometer and dropping funnel, and a mixture of 377.3 g of 95% diethyl thiodiacetate (1.74 mol) and 254 g of diethyl oxalate (1.74 mol) is subsequently added dropwise over the course of 60 minutes at from 0 to 20° C. The mixture is subsequently stirred for 2 hours at room temperature, for 1 hour at 40° C. and for 3 hours under reflux. The suspension is cooled, 47.6 g of potassium hydrogensulphate (0.35 mol) are added, and the mixture is stirred for 10 minutes. 1700 g of N,N-dimethylformamide (DMF) and 200 g of dimethyl sulphoxide (DMSO) are added with stirring. The methanol is distilled off over a 10 cm column under a water-jet vacuum until the top temperature reaches 40° C. at 100 mbar. 27.6 g of potassium carbonate (0.2 mol) are added, and 168.4 g of 1,2-dichloroethane (1.7 mol) are added dropwise over the course of 2 hours at 80° C. The suspension is stirred for 2 hours at 100° C. and for 10 hours at 125° C. 48 g of 1,2-dichloroethane (0.48 mol) are subsequently added dropwise over the course of 1 hour at 125° C. The reaction is continued to completion over the course of 8 hours at from 130 to 135° C. After the mixture has been cooled to about 70° C., about 1030 g of DMF/1,2-dichloroethane mixture are distilled off under a water-jet vacuum. The reaction batch is cooled and stirred into 4 l of ice-water. After a subsequent stirring time of 30 minutes, the product is filtered off with suction.

The crude product is suspended once in about 1.5 l of water with stirring and filtered off with suction.

Yield (dried): 417 g=93% of theory (residual salt content not taken into account)

EXAMPLE 2

3,4-Ethylenedioxythiophene-2,5-dicarboxylic Acid (Combination of the 2nd and 3rd steps)

980 g of DMF, 78 g of DMSO and 296.2 g of potassium carbonate (2.15 mol) are introduced into a 4 l flask with plane ground joints fitted with reflux condenser with gas outlet, thermometer, stirrer and heatable dropping funnel. A solution of 409 g of the ester mixture from Example 1 (1.76 mol) and 212.4 g of 1,2-dichloroethane (2.14 mol) in 980 g of DMF (dissolved at 50° C.) is added dropwise over the course of 2 hours at from 80 to 90° C. ($CO_2$ evolution). The suspension is stirred for 2 hours at 100° C. and for 10 hours at 125° C. 49.5 g of 1,2-dichloroethane (0.5 mol) are subsequently added dropwise over the course of 1 hour at 125° C. The reaction is continued to completion over the course of 8 hours at from 130 to 135° C. After the mixture has been cooled to about 70° C., about 1700 g of DMF/1,2-dichloroethane mixture are distilled off under a water-jet vacuum. 1107 g of 15% sodium hydroxide solution (4.15 mol) are added dropwise with stirring over the course of 2 hours at from 50 to 60° C. Stirring is subsequently continued at 60° C. for 14 hours. After the mixture has been cooled, 2646 g of 10% sulphuric acid (2.7 mol) are added dropwise with ice cooling until a pH of 1 has been reached. After a subsequent stirring time of 1 hour, the product is filtered off with suction. The crude product is suspended in 3 l of water and filtered off with suction. The product is dried at 80° C. for 24 hours and subsequently in a vacuum drying cabinet (80° C.) to constant weight.

Yield: 369.1 g=91% of theory (residual salt content not taken into account)

EXAMPLE 3

3,4-Ethylenedioxythiophene-2,5-dicarboxylic Acid (Combination of the 1st to 3rd steps)

1181.2 g of 32% potassium methoxide solution (5.4 mol) and 300 g of methanol are introduced into a 6 l apparatus with plane ground joints, fitted with a gate-impeller stirrer, reflux condenser, thermometer and dropping funnel, and a mixture of 552.9 g of 95% diethyl thiodiacetate (2.55 mol) and 372.3 g of diethyl oxalate (2.55 mol) is subsequently added dropwise over the course of 60 minutes at from 0 to 20° C. The mixture is subsequently stirred for 2 hours at room temperature, for 1 hour at 40° C. and for 3 hours under reflux. The suspension is cooled, 42 g of potassium hydrogensulphate (0.35 mol) are added, and the mixture is stirred for 10 minutes. 2500 g of DMF and 250 g of DMSO are added with stirring. The methanol is distilled off over a 10 cm column under a water-jet vacuum until the top temperature reaches 40° C. at 100 mbar. 37.5 g of potassium carbonate (0.27 mol) are added, and 233.5 g of 1,2-dichloroethane (2.36 mol) are added dropwise over the course of 2 hours at 80° C. The suspension is stirred for 2 hours at 100° C. and for 10 hours at 125° C. 155 g of 1,2-dichloroethane (1.56 mol) are subsequently added dropwise over the course of 1 hour at 125° C. The reaction is continued to completion over the course of 8 hours at from 130 to 135° C. After the mixture has been cooled to about 70° C., about 1800 g of DMF/1,2-dichloroethane mixture are distilled off under a water-jet vacuum. 3500 g of 15% sodium hydroxide solution (13.1 mol) are added dropwise with stirring over the course of 2 hours at from 50 to 60° C. Stirring is subsequently continued at 60° C. for 14 hours. After the mixture has been cooled, 7644 g of 10% sulphuric acid (7.8 mol) are added dropwise with ice cooling until a pH of 1 has been reached. After a subsequent stirring time of 1 hour, the product is filtered off with suction. The crude product is suspended in 3 l of water and filtered off with suction.

The product is dried at 80° C. for 24 hours and subsequently in a vacuum drying cabinet (80° C.) to constant weight.

Yield: 453.1 g=77% of theory (residual salt content not taken into account)

Although the present invention has been described in detail with reference to certain preferred versions thereof, other variations are possible. Therefore, the spirit and scope of the appended claims should not be limited to the description of the versions contained therein.

What is claimed is:

1. A process or e preparation of 3,4-alkylenedioxythiophene-2,5- dicarboxylic acid derivatives selected from the group consisting of compounds of the general formulae IV and V:

IV
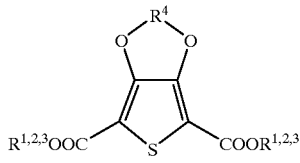

V
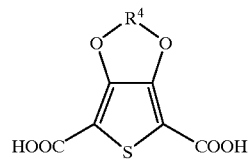

comprising carrying out at least 2 steps in accordance with formula scheme I without isolation of intermediates, wherein $R^1$, $R^2$, $R^3$ and $R^4$ are identical or different and are a linear or branched, optionally substituted alkyl radical having 1 to 20 carbon atoms, A is lithium, sodium or potassium, and Hal is fluorine, chlorine, bromine or iodine, wherein the formula scheme 1 comprises:

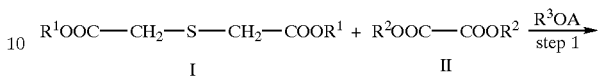

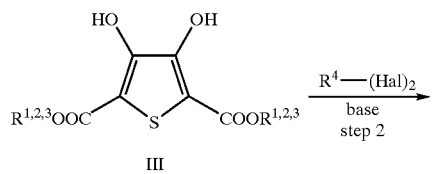

III

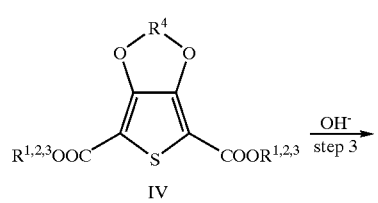

IV

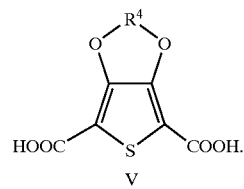

V

2. The process according to claim 1, wherein the dipotassium salt of the 3,4-dihydroxythiophene-2,5-dicarboxylic acid ester is employed in step 2.

3. The process according to claim 1, wherein step 2 is carried out in the presence of an excess of base.

4. The process according to claim 3, wherein the base used is potassium carbonate.

5. The process according to claim 1, wherein 3,4-ethylenedioxythiophene- 2,5-dicarboxylic acid is prepared.

* * * * *